US009863997B2

(12) United States Patent
Poluru et al.

(10) Patent No.: US 9,863,997 B2
(45) Date of Patent: Jan. 9, 2018

(54) DEVICES, METHODS, AND SYSTEMS FOR LOCALIZING A FAULT ON A LIVE CABLE

(71) Applicant: Honeywell International Inc., Morristown, NJ (US)

(72) Inventors: Venkat Poluru, Bengaluru (IN); Mahadevanna Basavaraj Shreshthi, Hubli (IN); Thappeta Peddaiah, Bangalore (IN); Zhenning Liu, Mississauga (CA); Sundeep Vanka, Bangalore (IN)

(73) Assignee: Honeywell International Inc., Morris Plains, NJ (US)

( * ) Notice: Subject to any disclaimer, the term of this patent is extended or adjusted under 35 U.S.C. 154(b) by 196 days.

(21) Appl. No.: 14/744,683

(22) Filed: Jun. 19, 2015

(65) Prior Publication Data
US 2016/0370419 A1    Dec. 22, 2016

(51) Int. Cl.
 G01R 31/08    (2006.01)
 G01N 27/04    (2006.01)
 G01R 35/00    (2006.01)

(52) U.S. Cl.
 CPC .......... *G01R 31/08* (2013.01); *G01N 27/046* (2013.01); *G01R 35/00* (2013.01)

(58) Field of Classification Search
 None
 See application file for complete search history.

(56) References Cited

U.S. PATENT DOCUMENTS

| 5,872,457 A | 2/1999 | Williams |
| 5,990,686 A | 11/1999 | Vokey et al. |
| 2007/0124093 A1* | 5/2007 | Choi .................... G01R 31/088 702/59 |
| 2009/0254297 A1* | 10/2009 | Bengtsson ............ G01R 27/16 702/117 |

(Continued)

FOREIGN PATENT DOCUMENTS

| JP | 2003035740 | 2/2003 |
| JP | 2012122752 | 6/2012 |

OTHER PUBLICATIONS

"Fault Finding Solutions". Megger. Accessed from http://www.cablejoints.co.uk./upload/Megger_Cable_Fault_Finding_Solutions.pdf on Jan. 16, 2015. 44 pages.

(Continued)

*Primary Examiner* — Jermele M Hollington
*Assistant Examiner* — Suresh K Rajaputra
(74) *Attorney, Agent, or Firm* — Brooks, Cameron & Huebsch, PLLC (57) ABSTRACT

Devices, methods, and systems for localizing a fault on a live cable are described herein. One system includes a wire fault localizer configured to receive current information from a location where direct current is applied to a cable comprising a number of loads, receive additional current information from at least two additional locations on the cable, wherein one of the at least two additional locations is on a source side of the cable and one of the at least two additional locations is on a load side of the cable, determine a fault resistance of the cable based on the received current information and received additional current information, and determine a fault distance on the cable based on the fault resistance.

20 Claims, 7 Drawing Sheets

(56) References Cited

U.S. PATENT DOCUMENTS

| | | | | |
|---|---|---|---|---|
| 2010/0215358 | A1* | 8/2010 | Harres | G01R 31/1227 398/17 |
| 2012/0086459 | A1 | 4/2012 | Kim | |
| 2014/0336959 | A1 | 11/2014 | Thomas et al. | |
| 2015/0015066 | A1* | 1/2015 | Dong | H02H 3/16 307/18 |
| 2016/0041216 | A1* | 2/2016 | Tang | H02H 3/38 324/509 |

OTHER PUBLICATIONS

Insulation Resistance Monitoring System (IRMS). ABD Airfield Solutions. 2010. Accessed from http://www.adb-air.com/Media/Documents/1162/96A0380.pdf. 34 pages.

Tobias Neier. "Cable Fault Location in LV, MV and HV Underground Cable Networks". Jun. 2009. Accessed from http://hvtechnologies.com/Portals/0/products/hv_brochures/Cable%20Fault%20Location%20Practical%20Experience.pdf. 59 pages.

* cited by examiner

DEVICES, METHODS, AND SYSTEMS FOR LOCALIZING A FAULT ON A LIVE CABLE

TECHNICAL FIELD

The present disclosure relates to devices, methods, and systems for localizing a fault on a live cable.

BACKGROUND

A cable fault can be caused by an insulation breakdown. The failure modes of such a cable fault can include a short circuit to ground and/or a "soft fault" with a relatively low electrical impedance (or resistance), comparing to that of the cable insulation, between the cable and the earth ground.

For example, in the case of the airfield lighting system, where each lighting segment may contain an array of 250 runway light assemblies coupled in series by a power cable buried in the runway which runs as much as 15 Kilometers, a power cable fault can lead to a large number of runway lights to go off, resulting in safety hazard and potentially part of the airport runways being shutdown. Sometimes, even if a power cable problem, such as the insulation deterioration, can be detected at its early stage through leakage current tests, no further, action can be taken due to lack of problem location information, until the problem gets further escalated to cause an actual damage.

As can be seen, there is a need for an effective cable problem detection method, and particularly a way to obtain the knowledge of the problem location, which not only can significantly shorten the time for cable maintenance, but also may effectively avoid actual damages as results of the cable fault by fixing the cable problem at its early stage.

DETAILED DESCRIPTION

Devices, methods, and systems for localizing a fault on a live cable are described herein. For example, one or more embodiments include a wire fault localizer configured to receive current information from a location where direct voltage is applied to a cable comprising a number of loads, receive additional current information from at least two additional locations on the cable, wherein one of the at least two additional locations is on a source side of the cable and one of the at least two additional locations is on a load side of the cable, determine a fault resistance of the cable based on the received current information and received additional current information, and determine a fault distance on the cable based on the fault resistance.

Localizing a fault on a live cable in accordance with the present disclosure can include determining a location of a fault in a circuit while loads on the circuit are provided with power. A number of examples herein reference an airport lighting systems. However, embodiments of this disclosure are not limited to these specific examples and can be utilized for other electrical systems that provide power to a number of loads.

A system for localizing a fault on a live cable in accordance with the present disclosure can utilize a wire fault localizer. The wire fault localizer can receive insulation resistance information from an insulation resistance measurement system (IRMS). In addition, the wire fault localizer can receive current information from a number of current sensors. In some examples, the wire fault localizer can receive current information from a first sensor at a location on the cable where direct current (DC) voltage is applied. The DC voltage can be applied between the cable and the earth ground to determine if there is a leakage current going from the cable to the earth ground. For example, a relatively high DC voltage (e.g., 540 V) can be applied to the cable system and leakage current as a result of the applied DC voltage can be monitored to determine whether the leakage current is greater than a threshold. In one example, leakage current that is greater than a threshold can indicate that there is a fault in the cable insulation. In another example, leakage current that is in between two thresholds can indicate that there is an insulation deterioration in the cable (i.e. a "soft fault") which may not immediately cause failures, but may need maintenance or repair at a convenient time at a relatively minimum cost. In yet another example, leakage current that is smaller than a threshold can indicate that the cable is in a healthy condition (e.g., functional condition, etc.).

The wire fault localizer can also receive current information from a sensor on a load side (e.g., side with a number of loads) of the location where the DC voltage is applied. In addition, the wire fault localizer can also receive current information from a sensor that is located on a source side of the location where the DC voltage is applied. In some examples, the current information from the number of sensors and the insulation resistance information can be utilized by the wire fault localizer to determine (e.g., calculate, etc.) a distance from a particular location on the cable system. Thus, the wire fault localizer can determine a precise location on the cable system where the fault is located.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that process changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits.

Figure 1:
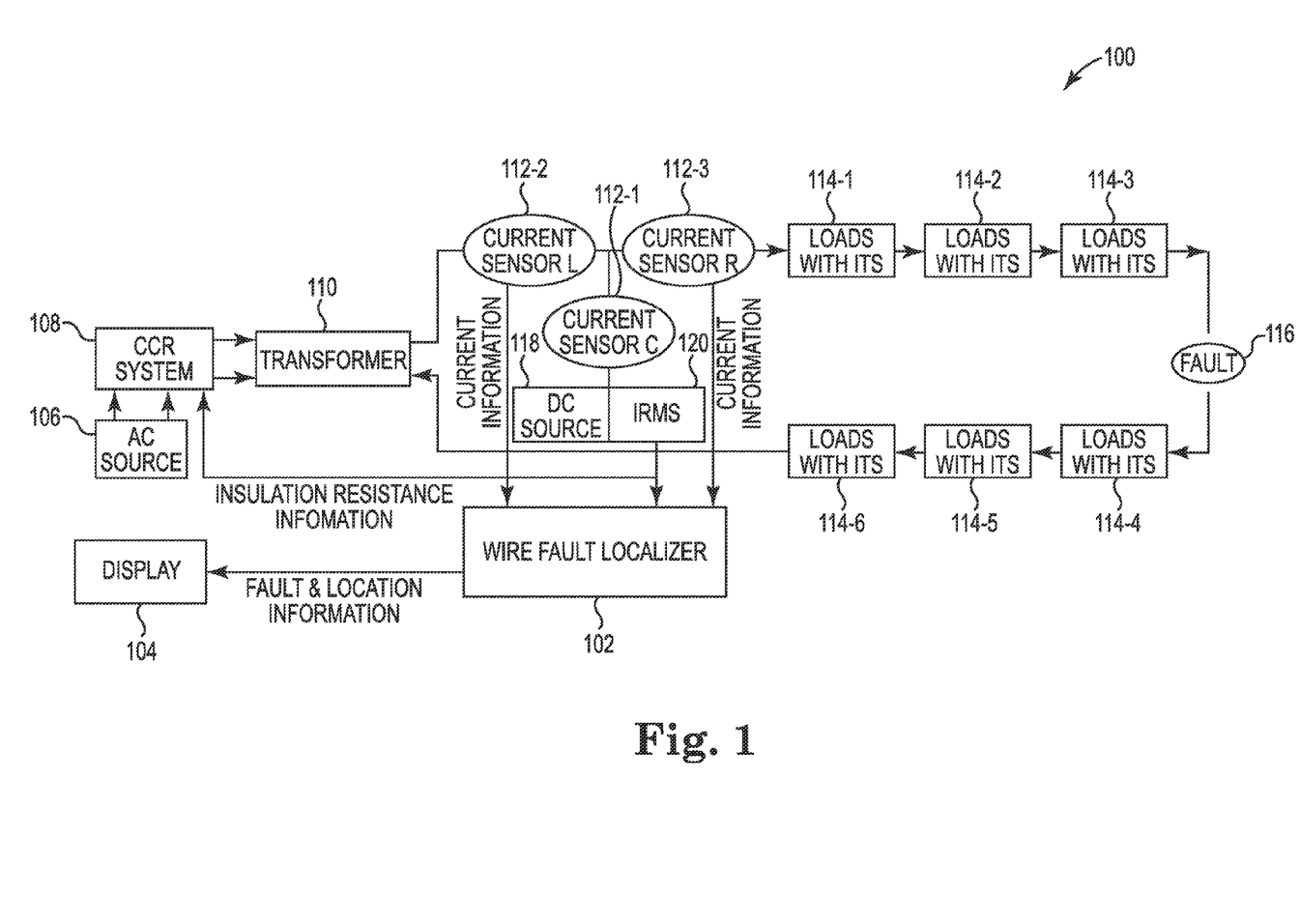
FIG. 1 is an example of a system for localizing a fault on a live cable according to one or more embodiments of the present disclosure.

FIG. 1 is an example of a system 100 for localizing a fault on a live cable according to one or more embodiments of the present disclosure. The system 100 can represent an electrical system such as a lighting system with a plurality of lights connected in series by a cable system. For example, the system 100 can represent an airport runway lighting system.

The system 100 can include an alternating current (AC) source 106 and constant current regulator (CCR) system 108 to provide AC voltage to a number of loads with isolation transformers (IT)s 114-1, 114-2, 114-3, 114-4, 114-5, 114-6. The system 100 can also include a transformer 110 to increase or decrease the voltage output of the AC source 106.

The number of loads with ITs 114-1, 114-2, 114-3, 114-4, 114-5, 114-6 can include a number of devices that can utilize the AC voltage from the AC source 106. For example, the number of loads with ITs 114-1, 114-2, 114-3, 114-4, 114-5, 114-6 can be runway lights with corresponding isolation transformers. Although the example illustrated in FIG. 1 includes six loads, embodiments of the present disclosure are not so limited.

The system 100 can include a direct current (DC) source 118 coupled to the cable system. The DC source 118 can apply a relatively high DC voltage to the cable system. The relatively high DC voltage can be utilized to determine if there is a fault 116 in the cable system. For example, the system 100 can monitor a DC current leakage of the cable system when the DC voltage is applied. The insulation resistance measurement system (IRMS) 120 can determine that a fault 116 is in the cable system (e.g., in the cable(s) of the system to which the number of loads are coupled, etc.) when the current leakage is greater than a threshold.

The IRMS 120 can send a notification to a wire fault localizer 102 when it is determined that there is a fault 116 in the cable system. The IRMS 120 and DC source 118 can be coupled to a location on the cable system. In some examples, the IRMS 120 and DC source 118 can be coupled to a location that is on a source side of the cable system.

The system 100 can include a number of current sensors 112-1, 112-2, 112-3. The number of current sensors 112-1, 112-2, 112-3 can be located at a number of locations on the cable system (e.g., each current sensor can be located at a different location on the cable system) and transmit current information from their respective locations to the wire fault localizer 102. The number of current sensors 112-1, 112-2, 112-3 can be utilized to measure a current of the DC voltage applied to the cable system via the DC source 118. As described further herein, the current information can be utilized by the wire fault localizer 102 to determine a location of the fault 116 (e.g., fault location, etc.). Although the example illustrated in FIG. 1 includes three sensors, embodiments of the present disclosure are not so limited.

In some examples, the current sensor 112-1 can be located at the same location or closely positioned near the location where the DC source 118 is coupled to the cable system. In addition, the current sensor 112-2 can be located on the cable system between the sensor 112-1 and the AC source 106. That is, the current sensor 112-2 can be located on the source side of the sensor 112-1. In addition, the current sensor 112-3 can be located on the cable system between the sensor 112-1 and the number of loads with ITs 114-1, 114-2, 114-3, 114-4, 114-5, 114-6. That is, the sensor 112-3 can be located on the load side of the sensor 112-1.

As used herein, the sensor 112-1 can be referred to as a center sensor (e.g., sensor C), the sensor 112-2 can be referred to as a left sensor (e.g., sensor L), and the sensor 112-3 can be referred to as a right sensor (e.g., sensor R). That is, the sensor 112-1 can be located between the sensor 112-2 and sensor 112-3.

The sensor information (e.g., current information, determined current through the cable, etc.) from the number of sensors 112-1, 112-2, 112-3 can be utilized to determine a resistance between the sensor 112-1 and the fault 116. The resistance between the sensor 112-1 and the fault 116 can be utilized to determine a distance between the sensor 112-1 and the fault 116. The distance between the sensor 112-1 and the fault 116 can be utilized to determine a relatively precise location of the fault on the cable system.

In some example, the system 100 can include a display 104 to display the sensor information and/or the location of the fault on the cable system. For example, the display 104 can display a location of a fault on an airfield lighting field utilizing airfield lighting model (example, graphical representation of lighting system which is equivalent to layout of lighting system. As described herein, determining a relatively precise location of the fault 116 can lower a time of repair and/or financial loss from the fault 116 interrupting the functionality of the system 100.

Figure 2:
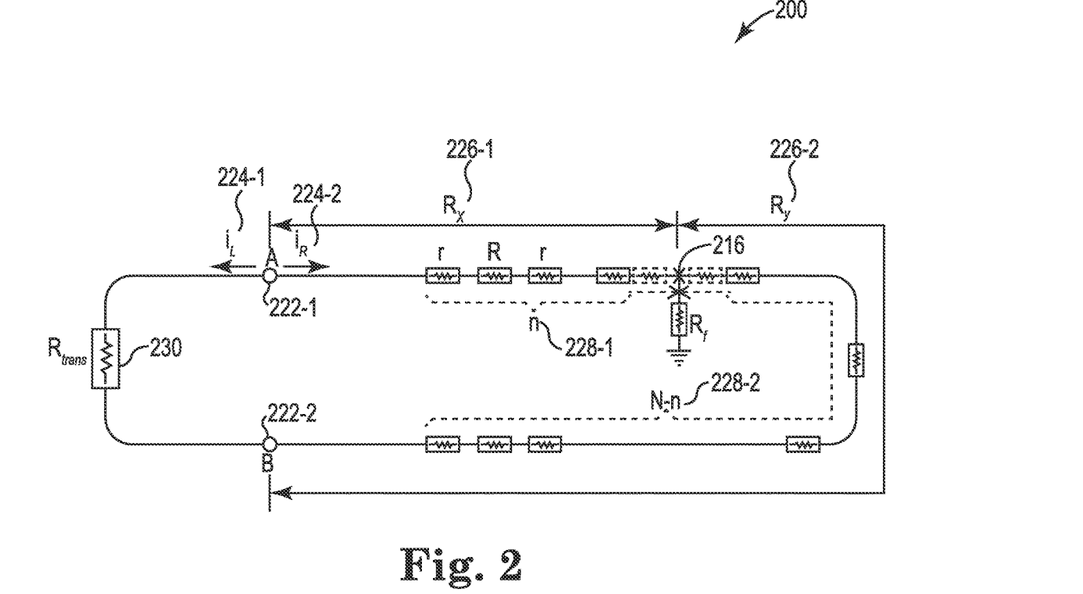
FIG. 2 is an example of a system model for localizing a fault on a live cable according to one or more embodiments of the present disclosure.

FIG. 2 is an example of a system 200 model for localizing a fault on a live cable according to one or more embodiments of the present disclosure. System 200 can be a representation of a similar electrical system such as an airport lighting system as system 100 referenced in FIG. 1.

The system 200 can include a number of designated locations 222-1, 222-2. In some examples, the designated location 222-1 can be a location where a DC source (e.g., DC source 118 as referenced in FIG. 1, etc.) is coupled to the cable system.

The system 200 can include current information 224-1, 224-2 from each side of the designated location 222-1. As described herein, the current information 224-1 can be determined by a sensor located on the cable between an AC source and the designated location 222-1. The current information 224-1 from the sensor located on the cable between the AC source and the designated location can be referenced as ($i_L$). The current information 224-2 can be determined by a sensor located on the cable between the designated location 222-1 and a number of loads 228-1. The current information 224-2 from the sensor located on the cable between the designated location 222-1 and the number of loads 228-1 can be referenced as ($i_R$).

The system 200 can include a number of loads 228-1 between the designated location 222-1 and a fault 216. Each of the number of loads 228-1 can include a particular resistance. For example, each of the number of loads 228-1 can include a lighting device and a corresponding isolation transformer (IT) that can place a load on the cable system. In some examples, the number of loads 228-1 between the designated location 222-1 and the fault 216 can be represented by (n).

The system 200 can include a number of loads 228-2 between the designated location 222-2 and the fault 216. The number of loads 228-2 can be similar loads as the number of loads 228-1. The number of loads 228-2 can be represented by (N−n) where (N) is a total number of loads for the cable system.

The system 200 can include a transformer resistance ($R_{trans}$) 230. The transformer resistance 230 can include a resistance that is caused by the transformer coupled to the cable system. The system 200 can include a resistance ($R_x$) 226-1. The resistance 226-1 can represent a resistance from the designated location 222-1 and the fault 216. The system 200 can also include a resistance ($R_y$) 226-2. The resistance 226-2 can represent a resistance from the designated location 222-2 and the fault 216. The fault 216 can have a particular resistance ($R_f$).

The particular resistance ($R_f$) of the fault 216 can correspond to a type of fault. For example, a soft fault and a short circuit can each have a corresponding level of resistance ($R_f$) that can be used to identify the type of fault.

The system 200 and corresponding values of resistance and current can be utilized to localize the fault 216. For example, the resistance and current information can be utilized to determine a distance between the designated location 222-1 and the fault 216.

Figure 3:
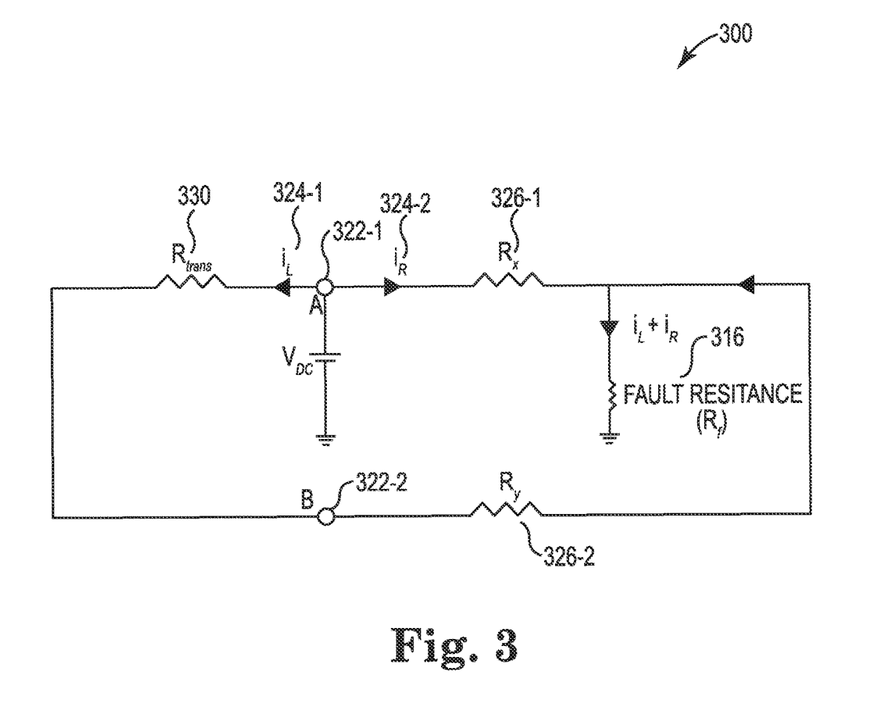
FIG. 3 is an example of an equivalent system model for localizing a fault on a live cable according to one or more embodiments of the present disclosure.

FIG. 3 is an example of an equivalent system 300 model for localizing a fault on a live cable according to one or more embodiments of the present disclosure. The system 300 can be a simplified representation of system 100 as referenced in FIG. 1 and/or system 200 as referenced in FIG. 2.

The system 300 can include a number of designated locations 322-1, 322-2. As described herein, the designated location 322-1 can be a location where a DC voltage ($V_{DC}$) is applied to the cable system. As described herein, a current sensor can be located at the designated location 322-1 to monitor current information from the designated location 322-1. The system 300 can also include a transformer resistance ($R_{trans}$) 330 that can include resistance caused by a transformer coupled to the cable system as described in reference to FIG. 1.

The system 300 can include current information 324-1, 324-2 that can be determined by a number of current sensors as described herein. The current information 324-1, 324-2 can include current information ($i_L$) 324-1 on a source side of the designated location 322-1 and current information ($i_R$) 324-2 on a load side of the designated location 322-1.

The system 300 can also include a resistance ($R_x$) 326-1 and a resistance ($R_y$) 326-2. The resistance ($R_x$) 326-1 can represent a resistance between the designated location 322-1 and the fault 316 with a fault resistance ($R_f$). The resistance ($R_y$) 326-2 can represent a resistance between the designated location 322-2 and the fault 316. In some examples, the current at the fault 316 can equal a sum of the current information ($i_L$) 324-1 and the current information ($i_R$) 324-2 (e.g., $i_L + i_R$).

Figure 4:
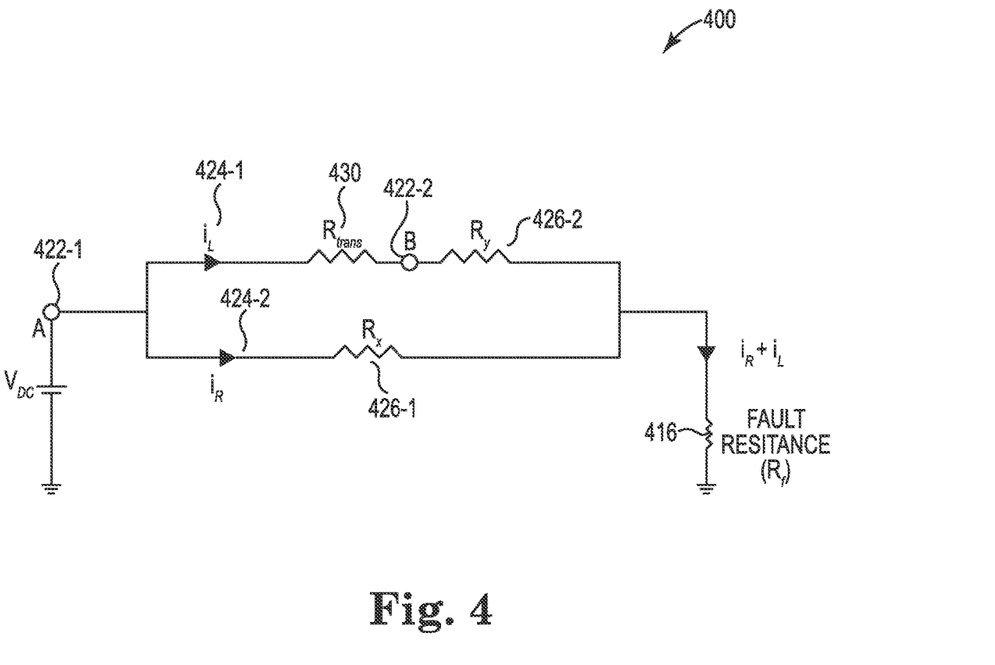
FIG. 4 is an example of an equivalent system model for localizing a fault on a live cable according to one or more embodiments of the present disclosure.

FIG. 4 is an example of an equivalent system 400 model for localizing a fault on a live cable according to one or more embodiments of the present disclosure. The system 400 can be a simplified representation of system 100 as referenced in FIG. 1, system 200 as referenced in FIG. 2, and/or system 300 as referenced in FIG. 3.

The system 400 can be a representation from the perspective of a designated location 422-1. In some examples, the designated location 422-1 can be a location where a DC voltage ($V_{DC}$) is applied to the cable system.

The system 400 can include current information 424-1, 424-2 on each side of the designated location 422-1. The current information 424-1 can be current information from a sensor that is located between the designated location 422-1 and an AC source/transformer. Thus, the current information 424-1 can be current information from a sensor that is located between the designated location 422-1 and the transformer resistance ($R_{trans}$) 430. The current information 424-2 can be current information from a sensor that is located between the designated location 422-1 and a number of loads.

System 400 can include a resistance (Rx) 426-1. The resistance 426-1 can be a resistance of the cable system between the designated location 422-1 and the fault 416. That is, the resistance 426-1 can include a resistance of a number of loads between the designated location 422-1 and the fault 416 and/or the fault resistance ($R_f$). The resistance ($R_y$) 426-2 can be a resistance of the cable system between the designated location 422-2 and the fault 416. The resistance 426-2 can include a resistance of a number of loads between the designated location 422-2 and the fault 416 with the fault resistance ($R_f$).

Figure 5:
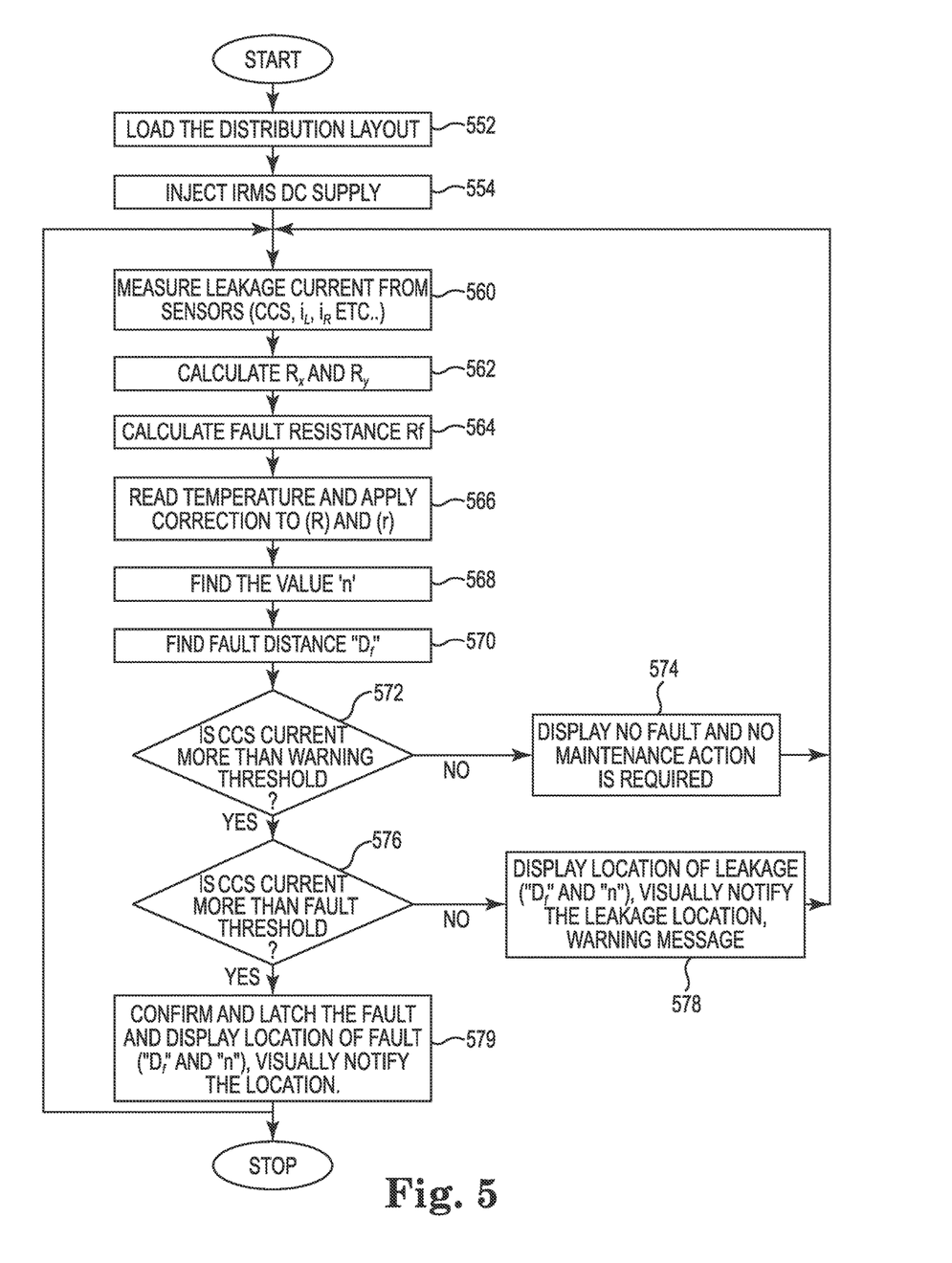
FIG. 5 is an example of a method for localizing a fault on a live cable according to one or more embodiments of the present disclosure.

FIG. 5 is an example of a method 550 for localizing a fault on a live cable according to one or more embodiments of the present disclosure. The method 550 can be performed by a computing device as described herein to localize a fault on a live cable.

The method 550 can include loading the distribution layout of a cable system (e.g., airfield lighting system, etc.) at block 552. Loading the distribution layout can include, but is not limited to: determining a location of a number of loads on a cable, determining a location of a number of current sensors, determining a location of a DC source, and/or determining a location of an AC source. The distribution layout can include information relating to an electrical system. For example, the distribution layout can include information relating to an airport lighting system. In this example, the distribution layout can include a distance between each of the runway lights on the airport lighting system, a resistance of the cable coupling the runway lights, among other features of the airport lighting system.

The method 550 can include injecting DC voltage via an insulation resistance measurement system (IRMS) at block 554. Injecting DC voltage can include applying a relatively high DC voltage to an electrical system. The electrical system can utilize an AC power source to provide electrical energy to the number of loads. For example, the electrical system can be an airport lighting system with a plurality of lights. In this example, the plurality of lights can be powered by an AC power source coupled to the plurality of lights. In addition, this example can include an IRMS to inject DC voltage to the airport lighting system. DC voltage can be injected in the presence or absence of AC power.

The method 550 can include measuring leakage current from sensors (e.g., CCS, $i_L$, $i_R$, etc.) at block 560. Measuring the leakage current can include determining a quantity of leakage current from the injected DC supply. In some embodiments, measuring leakage current from the sensors can include utilizing a prognostic method to determine resistance degradation of the cable. That is, the prognostic method can be utilized to determine a degradation level (e.g., rate of degradation of the cable, etc.) for the cable. The prognostic method can be utilized to avoid a complete shutdown of the lighting system by notifying a user that a portion of the cable is degrading at a particular rate so that the portion of the cable can be repaired before a complete shutdown is necessary for the repair.

The method 550 can also include measuring current information ($i_L$) from a left current sensor (LCS) and measuring current information ($i_R$) from a right current sensor (RCS). As described herein, the current information from the LCS can be represented as $i_L$ and the current information from the RCS can be represented as $i_R$. The current information can be a measured current for a particular portion of the cable system as described herein.

The method 550 can include determining (e.g., calculating) a first resistance ($R_x$) between a first point and the fault and determining a second resistance ($R_y$) between a second point and the fault at 562. In some examples, the first point can be a location where a DC voltage is injected via the IRMS. For example, the first point can be the same or similar position as location 222-1 as referenced in FIG. 2. In this example, the first resistance can be represented by resistance ($R_x$) 226-1 as referenced in FIG. 2. In another example, the second point can be the same or similar position as location 222-2 as referenced in FIG. 2. In this example, the second resistance can be represented by resistance ($R_y$) 226-2 as referenced in FIG. 2.

Determining the second resistance ($R_y$) can include utilizing Equation 1. Equation 1 can be based on a relationship between the first resistance ($R_x$) and the second resistance ($R_y$). For example, the sum of the first resistance ($R_x$) and the second resistance ($R_y$) can equal a total resistance of the cable ($R_{xy}$). The total resistance ($R_{xy}$) can be the actual resistance of the cable that covers the layout of the lighting system and can be measured under no fault conditions.

$$R_y = \left[\frac{i_R R_{xy} - i_L R_{trans}}{i_R + i_L}\right]$$ Equation 1

Equation 1 includes utilizing the current information ($i_R$) from the RCS, the current information ($i_L$) from the LCS, the transistor resistance ($R_{trans}$), and the total cable resistance ($R_{xy}$). When the second resistance ($R_y$) is determined utilizing Equation 1, the first resistance ($R_x$) can be determined from Equation 2.

$$R_x = R_{xy} - R_y$$ Equation 2

When the first resistance (Rx) and the second resistance (Ry) are determined, the method 550 can include determining a fault resistance ($R_f$) at block 564. The fault resistance (Rf) can be determined utilizing Equation 3.

$$R_f = \left[\frac{V_{dc} + i_R R_x}{i_{LR}}\right]$$ Equation 3

Equation 3 can determine the fault resistance ($R_f$) utilizing the injected DC voltage ($V_{dc}$), the current information from the RCS, the first resistance ($R_x$) and the sum of the current information from the RCS and the LCS ($i_{LR}$). When the fault resistance ($R_f$) is determined the method 550 can include reading temperatures and applying a temperature correction to a load resistance (r) and/or applying a temperature correction to a cable resistance (R) between each of the number of loads at block 566. In some examples, applying the temperature correction for the load resistance (r) can include utilizing Equation 4.

$$r = r_0(1+\alpha_0(t-t_0))$$ Equation 4

Equation 4 can be utilized to apply the temperature correction of an original load resistance ($r_0$) at an original temperature ($t_0$) by utilizing a monitored temperature (t) and a temperature coefficient ($\alpha_0$) of the cable connecting the number of loads. In some examples, applying the temperature correction for the cable resistance (R) can include utilizing Equation 5.

$$R = R_0(1+\alpha_0(t-t_0))$$ Equation 5

Equation 5 can be utilized to apply the temperature correction of an original cable resistance ($R_0$) at an original temperature ($t_0$) by utilizing a monitored temperature (t) and a temperature coefficient ($\alpha_0$) of the cable connecting the number of loads. In some examples, the method 550 can include determining a number of loads (n) from the location where DC voltage is injected into the cable system and the fault at block 568. In some examples, the number of loads (n) can be determined utilizing Equation 6.

$$R_x = nr + (n-1)R$$ Equation 6

Equation 6 can be utilized to determine the number of loads (n) by utilizing the first resistance ($R_x$), the temperature corrected load resistance (r), and temperature corrected cable resistance (R). Utilizing the first resistance ($R_x$), the temperature corrected load resistance (r), and temperature corrected cable resistance (R) can allow the number of loads (n) to be determined utilizing Equation 6. The determined number of loads (n) can be utilized to determined the fault distance ($D_f$) at block 570. In some examples, the fault distance ($D_f$) can be determined by determining a fault cable resistance ($R_{fc}$) utilizing Equation 7. In some examples, temperature correction may not be applied if the resistance variation is negligible.

$$R_{fc} = R_x - (n*r)$$ Equation 7

Equation 7 can utilize the calculated first resistance ($R_x$), the calculated number of loads (n), and the calculated temperature corrected load resistance (r) to calculate the fault cable resistance ($R_{fc}$). The fault cable resistance ($R_{fc}$) can be utilized to calculate the fault distance ($D_f$). The fault distance ($D_f$) can be calculated utilizing Equation 8.

$$D_f = \frac{R_{fc}}{\rho}$$ Equation 8

Equation 8 can utilize the fault cable resistance ($R_{fc}$) and a cable resistivity at a measure temperature ($\rho$). In some examples, the fault distance ($D_f$) can be a distance from the location where the DC voltage is injected to the location of the fault.

The method 550 can determine if current information from a center current sensor (CCS) is more (e.g., greater) than a warning threshold at block 572. The CCS can include a current sensor that is located at a location on the cable system where the DC voltage is injected via the IRMS. The current information from the CCS can be utilized to determine DC current leakage of the injected DC voltage. When the current leakage is less than a warning threshold the method 550 may display no fault and no maintenance action is required at block 574.

When the current leakage is greater than a warning threshold value the method can move to block 576 and determine if the CCS current is greater than a fault threshold. When the CCS current is greater than a fault threshold it can be determined that there is a fault in the cable system coupling the number of loads at block 579. When the current leakage is less than the fault threshold threshold value it can be determined that there is no fault at block 578. In some embodiments, the method 550 at block 578 can display a location of the leakage, visually notify a user of the leakage, and/or send a warning message to a user. In some embodiments, a fault can be determined based on a plurality of repetitive measurements and validation of the measurements.

In some examples, the method 550 can include displaying the fault location based on the fault distance ($D_f$) and number of loads (n) at block 572. In some examples, a visual representation of the lighting system can be displayed on a user interface and a location of the fault based on the fault distance ($D_f$) can be displayed on the user interface display.

Figure 6:
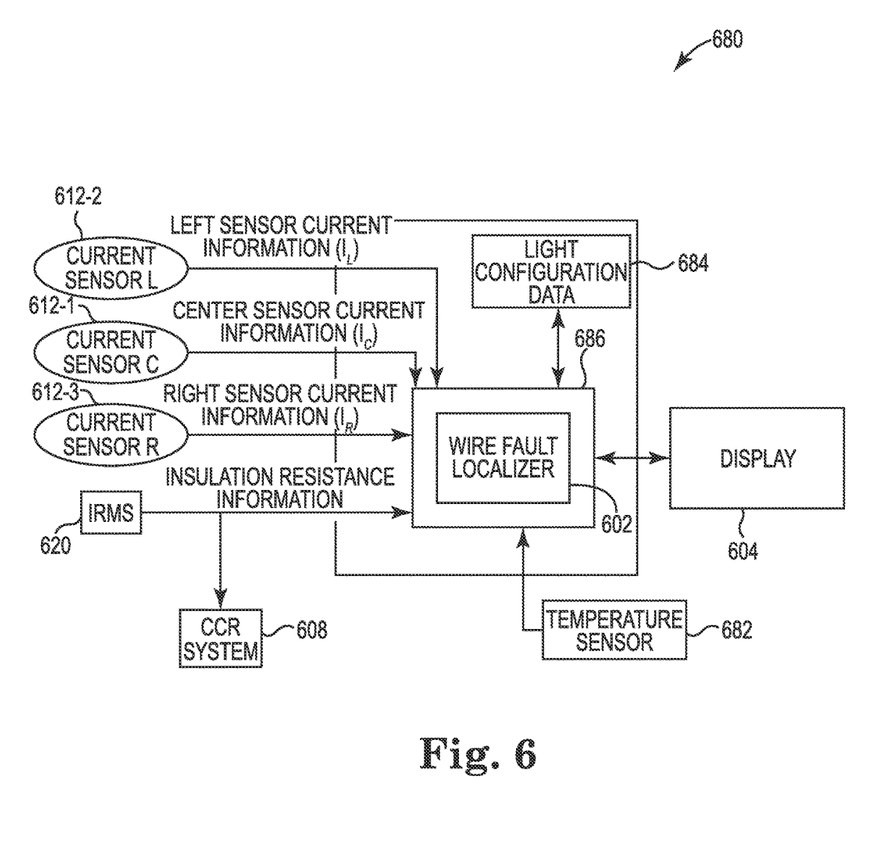
FIG. 6 is an example of a system for localizing a fault on a live cable according to one or more embodiments of the present disclosure.

FIG. 6 is an example of a system 680 for localizing a fault on a live cable according to one or more embodiments of the present disclosure. The system 680 can include a wire fault localizer 602 that includes a computing device 686 as described herein. The wire fault localizer 602 can be coupled to a display 604 (e.g., user interface, etc.).

The display 604 can display an electrical system such as an airport lighting system as described herein. The information received by the wire fault localizer and the information determined by the wire fault localizer 602 can be displayed on the display 604. For example, insulation resistance information from the insulation resistance measurement system (IRMS) 620 can be displayed on the display 604. In another example, a fault location based on monitored current information from a number of current sensors 612-1, 612-2, 612-3 can be displayed on a representation of the electrical system via the display 604.

In some examples, the computing device 686 can be coupled to the number of current sensors 612-1, 612-2, 612-3. As described herein, the number of current sensors 612-1, 612-2, 612-3 can be placed at specific locations on a cable system to receive current information at the specific locations.

In some examples, the computing device 686 can be coupled to the IRMS 620 and CCR system 608. As described herein, the IRMS 620 and CCR system 608 can be utilized to provide insulation resistance information to the computing device 686 for the wire fault localizer 602.

In some examples, the computing device 686 can be coupled to a temperature sensor 682. The temperature sensor 682 can provide exterior temperature information for an area where the cable electrical system is located. In some examples, the temperature sensor 682 can provide temperature information for the cable of the cable system. As described herein, the temperature information can be utilized to apply a temperature correction to determined resistance values of the cable system.

In some examples, the computing device 686 can receive lighting configuration data 684 for a lighting system such as an airport lighting system. The lighting configuration data 684 can include structural information of the lighting system. For example, the lighting configuration data can include a distance between each of a plurality of lights or group of lights, a resistance of the cable coupling the plurality of lights or group of lights, and/or a technical or non-technical specification/information relating to the lighting system.

Figure 7:
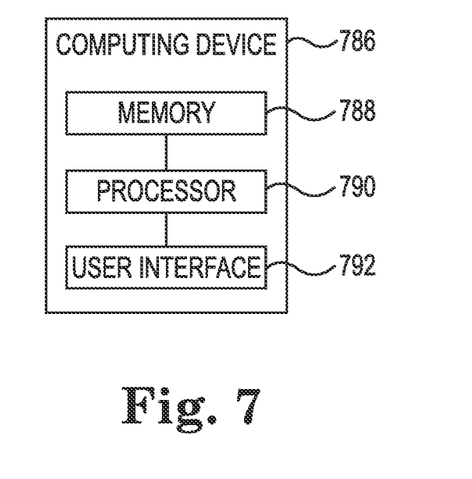
FIG. 7 is an example of a computing device for localizing a fault on a live cable according to one or more embodiments of the present disclosure.

FIG. 7 is an example of a computing device for localizing a fault on a live cable according to one or more embodiments of the present disclosure. Computing device 786 can be, for example, a laptop computer, a desktop computer, a micro-processing resource, or a mobile device (e.g., a mobile phone, a personal digital assistant, etc.), among other types of computing devices or embedded system. Computing device 786 can be utilized in systems 100, 200, 300, 400, and/or 680 to perform the functions previously described herein. For example, computing device 786 can be included in a wire fault localizer (e.g., wire fault localizer 102, wire fault localizer 602, light configuration data 684, display 604, etc.) used to localize a fault on a live cable in accordance with the present disclosure. Display 604 can be independent or integrated as part of computing device 786.

As shown in FIG. 7, computing device 786 includes a memory 788 and a processing resource 790 (e.g., processor) coupled to memory 788. Memory 788 can be any type of storage medium that can be accessed by processing resource 790 to perform various examples of the present disclosure. For example, memory 788 can be a non-transitory computer readable medium having computer readable instructions (e.g., computer program instructions) stored thereon that are executable by processing resource 790 to perform localizing a fault on a live cable in accordance with one or more embodiments of the present disclosure.

Memory 788 can be volatile or nonvolatile memory. Memory 788 can also be removable (e.g., portable) memory, or non-removable (e.g., internal) memory. For example, memory 788 can be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disc read-only memory (CD-ROM)), flash memory, a laser disc, a digital versatile disc (DVD) or other optical disk storage, and/or a magnetic medium such as magnetic cassettes, tapes, or disks, among other types of memory.

Further, although memory 788 is illustrated as being located in computing device 786, embodiments of the present disclosure are not so limited. For example, memory 788 can also be located internal to another computing resource (e.g., enabling computer readable instructions to be downloaded over the Internet or another wired or wireless connection).

As shown in FIG. 7, computing device 786 can also include a user interface 792. User interface 792 can include, for example, a display (e.g., a screen). The display can be, for instance, a touch-screen (e.g., the display can include touch-screen capabilities). User interface 792 (e.g., the display of user interface 792) can provide (e.g., display and/or present) information to a user of computing device 786.

Additionally, computing device 786 can receive information from the user of computing device 786 through an interaction with the user via user interface 792. For example, computing device 786 (e.g., the display of user interface 792) can receive input from the user via user interface 792. The user can enter the input into computing device 786 using, for instance, a mouse and/or keyboard associated with computing device 786, or by touching the display of user interface 792 in embodiments in which the display includes touch-screen capabilities (e.g., embodiments in which the display is a touch screen).

As used herein, "a" or "a number of" something can refer to one or more such things. For example, "a number of resources" can refer to one or more resources. Additionally, the designator "N", as used herein, particularly with respect to reference numerals in the drawings, indicates that a number of the particular feature so designated can be included with a number of embodiments of the present disclosure.

As described herein, a "module" can include computer readable instructions that can be executed by a processing resource to perform a particular function. A module can also include hardware, firmware, and/or logic that can perform a particular function.

As used herein, "logic" is an alternative or additional processing resource to execute the actions and/or functions, described herein, which includes hardware (e.g., various forms of transistor logic, application specific integrated circuits (ASICs)), as opposed to computer executable instructions (e.g., software, firmware) stored in memory and executable by a processing resource.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above elements and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A system for localizing a fault on a live cable, comprising:
    a wire fault localizer configured to:
        receive current information from a location where direct current is applied to a cable comprising a number of loads;
        receive additional current information from at least two additional locations on the cable, wherein one of the at least two additional locations is on a source side of the cable and one of the at least two additional locations is on a load side of the cable, and wherein the source side of the cable is a location between the location where direct current is applied and a source of alternating current, and the load side of the cable is a location between the location where direct current is applied and the number of loads;
        determine a fault resistance of the cable based on the received current information and received additional current information; and
        determine a fault distance on the cable based on the fault resistance.

2. The system of claim 1, wherein the fault distance is a distance from the location of the applied direct current on the cable to a location of a fault on the cable.

3. The system of claim 1, wherein the wire fault localizer is configured to apply a correction to the fault resistance based on a temperature of the cable or atmosphere.

4. The system of claim 1, wherein the wire fault localizer is configured to determine a number of load devices between a location of a fault on the cable and the location of applied direct current on the cable.

5. The system of claim 4, wherein the number of load devices are connected in series on the cable.

6. The system of claim 1, wherein the wire fault localizer is configured to determine the fault distance when the cable is powered by an alternating current (AC) source.

7. A non-transitory computer readable medium having computer readable instructions stored thereon that are executable by a processor to:
    receive current information from a sensor at a location where direct current is applied to a cable, a sensor on a source side of the location, and a sensor on a load side of the location wherein the source side of the location is a location between where direct current is applied and a source of alternating current, and the load side of the location is between where direct current is applied and a number of loads on the cable;
    determine a first resistance from a first point on the cable to a fault location on the cable based on the received current information;
    determine a second resistance from a second point on the cable to the fault location based on the received current information; and
    determine a fault distance from the first point to the fault location based on the first resistance, the second resistance, and a quantity of the number of loads on the cable.

8. The medium of claim 7, comprising instructions executable by the processor to apply a temperature correction to the first and second resistance.

9. The medium of claim 7, comprising instructions executable by the processor to determine a cable distribution layout of the cable.

10. The medium of claim 9, wherein the cable distribution layout includes a number of devices creating the number of loads on the cable, a distance between each of the number of devices, and a cable resistivity at a particular temperature.

11. The medium of claim 7, comprising instructions executable by the processor to determine an existence of a fault on the cable based on a comparison of a current of the cable to a threshold value.

12. The medium of claim 7, wherein the first resistance is determined by dividing a difference between a voltage of the cable and a transformer voltage by a sum of received current information from the sensor on the source side and the sensor on the load side.

13. The medium of claim 12, wherein the voltage of the cable is a product of the received current information from the sensor on the load side and a resistance of the cable.

14. The medium of claim 12, wherein the transformer voltage is a product of the received current information from the sensor on the source side and a transformer secondary resistance.

15. A method for localizing a fault on a live cable, comprising:
    determining a voltage of a cable based on a resistance of the cable and a current received from a sensor on a load side of a location for applying direct current (DC) voltage to the cable wherein the load side of the location is between where direct current is applied to the cable and a number of loads on the cable;
    determining a transformer voltage based on a transformer secondary resistance and a current received from a sensor located on a source side of the location for applying DC voltage to the cable, wherein the source side of the location is a location between where direct current is applied to the cable and a source of alternating current;

determining a fault resistance of the cable based on the voltage of the cable and the transformer voltage; and determining a fault distance based on the fault resistance.

16. The method of claim 15, comprising determining a location of the fault on the cable based on the fault distance.

17. The method of claim 15, wherein the fault resistance is determined by a sum of the DC voltage and the cable voltage divided by the sum of first and second current and wherein the fault resistance includes a resistance degradation of the cable over a period of time.

18. The method of claim 15, wherein the fault distance is calculated by dividing the fault resistance by a resistivity of the cable.

19. The method of claim 15, comprising determining a current at the fault based on a sum of the current received from the sensor located on the source side and the current received from the sensor located on the load side.

20. The method of claim 15, wherein the live cable is part of an airport lighting system.

* * * * *